(12) United States Patent
Asou et al.

(10) Patent No.: US 11,160,816 B2
(45) Date of Patent: Nov. 2, 2021

(54) COMPOSITION FOR TREATMENT OF ALZHEIMER'S DISEASE

(71) Applicant: GLOVIA COMPANY LIMITED, Tokyo (JP)

(72) Inventors: Hiroaki Asou, Tokyo (JP); Hiroaki Murase, Tokyo (JP)

(73) Assignee: GLOVIA COMPANY LIMITED, Tokyo (JP)

( * ) Notice: Subject to any disclaimer, the term of this patent is extended or adjusted under 35 U.S.C. 154(b) by 0 days.

(21) Appl. No.: 16/604,880

(22) PCT Filed: Mar. 30, 2018

(86) PCT No.: PCT/JP2018/013549
§ 371 (c)(1),
(2) Date: Oct. 11, 2019

(87) PCT Pub. No.: WO2018/190146
PCT Pub. Date: Oct. 18, 2018

(65) Prior Publication Data
US 2020/0179414 A1 Jun. 11, 2020

(30) Foreign Application Priority Data
Apr. 12, 2017 (JP) .............................. JP2017-079106

(51) Int. Cl.
| | | |
|---|---|---|
| *A61K 31/685* | (2006.01) | |
| *A23L 33/105* | (2016.01) | |
| *A61P 25/28* | (2006.01) | |
| *A61K 31/7048* | (2006.01) | |
| *A61K 36/752* | (2006.01) | |

(52) U.S. Cl.
CPC .......... *A61K 31/685* (2013.01); *A23L 33/105* (2016.08); *A61K 31/7048* (2013.01); *A61K 36/752* (2013.01); *A61P 25/28* (2018.01); *A23V 2002/00* (2013.01)

(58) Field of Classification Search
None
See application file for complete search history.

(56) References Cited

U.S. PATENT DOCUMENTS

2009/0176740 A1\* 7/2009 Phillips, II ......... A61K 31/4015
514/75

FOREIGN PATENT DOCUMENTS

| EP | 1 203 584 A1 | 5/2002 |
| EP | 1203584 | \* 5/2002 |
| JP | 2008-127325 A | 6/2008 |
| KR | 2019 142464 | \* 12/2019 |

OTHER PUBLICATIONS

Sato N. et al. Administration of Chingi, A Component of Herbal Medicine. Evidence Based Complementary and Alternative Medicine vol. 2011, 1-9. (Year: 2011).\*
International Search Report, issued in PCT/JP2018/013549, dated Jun. 26, 2018.
Kudoh et al., "Effect of ninjin'yoeito, a Kampo (traditional Japanese} medicine, on cognitive impairment and depression in patients with Alzheimer's disease: 2 years of observation", Psychogeriatrics, 2016, vol. 16, Issue 2, pp. 85-92.
Kudoh et al., "The Mechanism of Ninjin-Youei-to (a Kampo Medicine) in Alzheimer's Disease", Journal of New Remedies & Clinics, 2015, vol. 64, No. 10, pp. 1072-1083.
Moreno, "Cognitive Improvement in Mild to Moderate Alzheimer's Dementia After Treatment with the Acetylcholine Precursor Choline Alfoscerate: A Multicenter, Double-Blind, Randomized, Placebo-Controlled Trial", Clin. Ther., 2003, vol. 25, Issue 1, pp. 178-193.
Morita et al., "Structure and biological function of ENPP6, a choline-specific glycerophosphodiester-phosphodiesterase", Scientific Reports, 2016, vol. 6, srep20995, pp. 1-14.
Sangiorgi et al., "alpha-Glycerophosphocholine in the Mental Recovery of Cerebral Ischemic Attacks", Ann. N. Y. Acad. Sci., 1994, vol. 717, Issue 1, pp. 253-269.
Sato et al., "Administration of Chinpi, a Component of Herbal Medicine Ninjin-Youei-To, Reverses Age-Induced Demyelination", Evidence-Based Complementary and Alternative Medicine, 2011, vol. 2011, Article ID 617438, pp. 1-9.
Seiwa et al., "Restoration of FcRgamma/Fyn Signaling Repairs Central Nervous System Demyelination", Journal of Neuroscience Research, 2007, vol. 85, Issue 5, pp. 954-966.
Tokunaga et al., "An Extract of Chinpi, the Dried Peel of the Citrus Fruit Unshiu, Enhances Axonal Remyelination via Promoting the Proliferation of Oligodendrocyte Progenitor Cells", Evidence-Based Complementary and Alternative Medicine, 2016, vol. 2016, Article ID 8692698, pp. 1-9.
Written Opinion of the International Searching Aurhotity, issued in PCT/JP2018/013549, dated Jun. 26, 2018.

\* cited by examiner

*Primary Examiner* — Ralph J Gitomer
(74) *Attorney, Agent, or Firm* — Birch, Stewart, Kolasch & Birch, LLP

(57) ABSTRACT

Provided is a composition for the treatment and/or prevention of Alzheimer's disease having an improved therapeutic or prophylactic effect together with reduced side effects. This composition for the treatment and/or prevention of Alzheimer's disease contains at least one compound selected from the group consisting of glycerophosphocholine (G) and pharmaceutically acceptable salts thereof as a first active ingredient and at least one compound selected from the group consisting of herperidin (H), narirutin (N), and pharmaceutically acceptable salts thereof as a second active ingredient. This composition promotes remyelination, promotes the activity of α-secretase, and also suppresses the expression of β-secretase.

4 Claims, 7 Drawing Sheets

COMPOSITION FOR TREATMENT OF ALZHEIMER'S DISEASE

TECHNICAL FIELD

The present invention relates to a composition for the treatment and/or prevention of Alzheimer's disease.

THE RELATED ART

As we are facing a super-aging society, the number of people with dementia who visit a medical institution is rapidly increasing. According to the World Alzheimer's Report 2015, there were 46.8 million people with dementia globally, and there will be 131.50 million people living with dementia worldwide by 2050. The number of people with dementia is approximately doubling every 20 years, and it has been warned that dementia is a disease that will bring about a global crisis. Therefore, the development of an effective method of prevention and an effective method of treatment for dementia has become imperative.

The cardinal symptom of Alzheimer's disease, the leading cause of dementia, is progressive dementia, but an increase in the number of senile plaques and neurofibrillary tangles in the brain as well as cerebral atrophy due to neuron deficit have been found to be pathological features. Considering these features, the degeneration or deficit of neurocytes in gray matter region has been considered a cause of Alzheimer's disease. That is, the senile plaque is formed by the condensation and deposition of amyloid β protein in the brain in accordance with the metabolic disorder of amyloid precursor protein (amyloid precursor protein is hereinafter referred to as "APP" and amyloid β protein is hereinafter referred to as "Aβ"), and it has been considered that this condensation and deposition of Aβ causes formation of neurofibrillary tangle, loss of neuron, and consequently, cognitive dysfunction. It has also been found that soluble Aβ oligomers that are formed in the process of the aggregation of Aβ are correlated with the decrease in nervous synapses that are closely related with the severity of dementia. Therefore, treatment and/or prevention of Alzheimer's disease for the purpose of reducing the expression amount of Aβ, especially soluble Aβ oligomers, has been vastly investigated.

On the other hand, however, it has been reported recently that an anomaly has been found in the white matter of Alzheimer patients' brain, where, especially, myelin is remarkably decreased, and the anomaly in the white matter has been found not only in the splenium of the corpus callosum which is the site of early myelination and the genu of the corpus callosum which is the site of later myelination, but also in the hippocampus CAI lower region; thus, it has been suggested that axonal degeneration or demyelination in white matter region may be a potentially important factor in mild cognitive dysfunction and in Alzheimer's disease. Therefore, treatment and/or prevention of Alzheimer's disease for the purpose of recovering from demyelination has been considered.

Nonpatent document 1 (J Neurosci Res. 85:954-966, 2007) reports that the amount of phosphorylated myelin basic protein, especially phosphorylated myelin basic protein having a molecular mass of 21.5 kDa (hereinafter, myelin basic protein is referred to as "MBP," phosphorylated MBP is referred to as "p-MBP," MBP having a molecular mass of X kDa is referred to as "XkDaMBP", and phosphorylated XkDaMBP is referred to as "p-XkDaMBP"), was remarkably decreased during the demyelination induced by aging and by the application of demyelination inducer cuprizone, and that a trigger molecule for myelin formation was an immunoglobulin Fc receptor, and the Fc receptor and a trigger molecule of Fyn become a signal to control the on and off of a small G protein (Rho), further activate MAPK as its effector, promote the phosphorylation of MBP, stratify a myelin membrane and maintain the compression of myelin. This document further reports that the recovery from demyelination in the cuprizone-treated mouse and the aged mouse was accomplished by the administration of Ninjin'yoeito and the Ninjin'yoeito can be an effective treatment targeting the FcRγ/Fyn-Rho(Rac 1)-MAPK(P38 MAPK)-p-MBP signaling cascade. This document further reports that the administration of Ninjin'yoeito to an aged mouse of 31 months old for 2 months decreased the G-ratio (the ratio of the diameter of an axon to the diameter of the axon and the surrounding myelin sheath) as a measure of demyelination progress from the pre-administration level of approximately 0.82 to approximately 0.73, where the recovery from demyelination was comparative to that of a 3-month-old mouse (G-ratio value: approximately 0.75) (see FIG. 1C of this document). Also, nonpatent document 2 (Psychogeriatrics 2015 [doi:10.1111/psyg.12125]) reports that, as a result of combined administration of Ninjin'yoeito for 24 hours to mild to moderate Alzheimer patients for whom donepezil is insufficiently effective, a significant improvement in cognitive performance maintenance and in depressed state has been found compared with a single administration group of donepezil.

Nonpatent document 3 (Evid Based Complement Alternative Med. 2011 [doi:10.1093/ecam/neq001]) reports that, out of 12 kinds of galenicals that constitute Ninjin'yoeito, Chinpi derived from Citrus unshiu was an active component to recover from demyelination due to aging, and recovery from demyelination was realized by not the repression of demyelination but the remyelination, and further reports that the cultivation of an oligodendrocyte progenitor cell that develops into myelin in the presence of hesperidin and/or narirutin which are principal components of the Chinpi promoted the generation of p-21.5kDaMBP and rapidly proceeded the proliferation and differentiation of the oligodendrocyte progenitor cell, in the same way as the cultivation of an oligodendrocyte progenitor cell in the presence of the Chinpi. Furthermore, patent document 1 (JP 2008-127325 A) proposes a p-MBP generation promoter comprising hesperidin and/or narirutin as active ingredients and its usage in the treatment and/or prevention of dementia. The Chinpi derived from Citrus unshiu is different than dried citrus peel derived from mandarin orange or other Citruses in that the former contains a larger amount of both hesperidin and narirutin.

Nonpatent document 4 (J. New Rem. & Clin. 2015; 64; 1072-1083) reports that, in the brain of a shiverer mouse with myelin hypoplasia due to the deletion of exon 3-7 of the MBP gene, the non-Aβ generation pathway was inhibited and the N-terminal fragment referred to as sAPPα, which is generated by α-secretase cleaving APP, did not develop, and that in the brain of an aged mouse to which Ninjin'yoeito was administered for 2 months, p-21.5kDaMBP was increased and at the same time soluble Aβ oligomers, which are derived from Aβ generated in the Aβ generation pathway, were significantly decreased, and based on the results of the abovementioned experiments, it is inferred that the Aβ generation pathway is repressed by the action of MBP, and therefore, the non-Aβ generation pathway is promoted, and the generation of soluble Aβ oligomers is repressed and sAPPα is generated. The Aβ generation pathway is a pathway in which β-secretase cleaves APP and generates the N-terminal fragment referred to as sAPPβ and the C-terminal fragment referred to as CTF-β, and then γ-secretase cleaves this fragment and generates Aβ and the APP intracellular domain (AICD), and the non-Aβ generation pathway is a pathway in which α-secretase cleaves APP and generates the N-terminal fragment referred to as sAPPα and the C-terminal fragment referred to as CTF-α, and then γ-secretase cleaves this fragment and generates p3 and AICD.

In addition, glycerophosphocholine, also referred to as α-GPC or L-α-glycerylphosphorylcholine (hereinafter glycerophosphocholine is referred to as "α-GPC") is a substance involved in myelination. The α-GPC is a natural compound contained in brain or in milk which is metabolized on the choline metabolism to choline by ENPP6, a choline-specific phosphodiesterase which exists on the cell membrane of oligodendrocyte as myelin-forming cell, and the choline generated is utilized for the lipid synthesis of oligodendrocyte and myelination then proceeds (see nonpatent document 5 [Scientific reports |6:20995|Doi: 10.1038/srep20995]). It is also known that the α-GPC has an improving effect on cognitive functions. For example, nonpatent document 6 (Ann N Y Acad Sci. 1994 Jun. 30; 717: 253-69) reports that administration of 1000 mg α-GPC per day for 28 days and subsequent oral administration of 400 mg α-GPC per day for 5 months to 2,044 stroke patients caused the recovery of the patients' cognitive abilities, and nonpatent document 7 (Clin Ther. 2003 January; 25(1): 178-93) reports that the administration of α-GPC in the amount of a 400 mg capsule 3 times per day to mild to moderate Alzheimer patients for 180 days gave an improving effect on cognitive function. Also, patent document 2 (EP 1203584 A1) suggests the concurrent use of an acetylcholinesterase inhibitor together with α-GPC.

Advantageous effects such as an improving effect on cognitive function as well as the promotion of growth hormone secretion, the improvement of liver injury, decrease in blood pressure or mitigation of decrease in choline concentration have been recognized in α-GPC, but harmful adverse drug reactions have also been reported. For example, nonpatent document 6 reports that harmful adverse drug reactions have been found in 2.14% of the patients, of which 0.7% was heartburn, 0.5% was vomiturition/emesis, 0.4% was insomnia/agitation and 0.2% was headache, and 0.7% of the patients hoped for stop of treatment. Therefore, the intake of a large amount of α-GPC should be avoided, though α-GPC is a natural compound that is found in a human body.

PRIOR ARTS DOCUMENTS

Patent Documents

Patent Document 1: JP 2008-127325 A
Patent Document 2: EP 1203584 A1

Nonpatent Documents

Nonpatent Document 1: J Neurosci Res. 85: 954-966, 2007
Nonpatent Document 2: Psychogeriatrics 2015 [doi: 10.1111/psyg.12125]
Nonpatent Document 3: Evid Based Complement Alternative Med. 2011 [doi: 10.1093/ecam/neq001]
Nonpatent Document 4: J. New Rem. & Clin. 2015; 64; 1072-1083
Nonpatent Document 5: Scientific reports |6:20995|Doi: 10.1038/srep20995
Nonpatent Document 6: Ann N Y Acad Sci. 1994 Jun. 30; 717: 253-69
Nonpatent Document 7: Clin Ther. 2003 January, 25(1); 178-93

SUMMARY OF THE INVENTION

Problems to be Solved by the Invention

As mentioned above, Ninjin'yoeito, or hesperidin and/or narirutin as active ingredients of Chinpi derived from Citrus unshiu, has a beneficial effect in that it promotes useful p-MBP generation, promotes remyelination and inhibits the generation of toxic soluble Aβ oligomers, so that effective treatment and/or prevention of Alzheimer's disease may be expected by using thereof. However, further improvement in the effects of treatment and/or prevention has been always requested, and at the same time, harmful adverse drug reactions should be avoided.

Therefore, the purpose of the present invention is to offer a composition of the treatment and/or prevention for Alzheimer's disease that can meet the abovementioned request.

Means for Solving Problems

The inventors have given a more detailed examination into the relationship between MBP generation and sAPPα generation shown in nonpatent document 4. As a pathological mouse model for Alzheimer's disease, the gene modified mouse Tg2576 which Swedish mutant human APP ($APP_{K670N/M671L}$) genes were introduced to (hereinafter referred to as a "Tg2576 mouse") was used to investigate the difference in the amount of p-MBP expression and the difference of the binding state of p-MBP with A Disintegrin and Metalloprotease (ADAM) 9, which is particularly known to show α-secretase activity among ADAMs, between the brain of young mice of 3 months and the brain of the aged mice of 28 months. It has been known that a large amount of Aβ is accumulated in the brain of aged mice of 28 months. The results of the investigation are shown below, and no expression of p-21.5kDaMBP was found, or no binding between ADAM9 and p-21.5kDaMBP was found in the brain of the aged mice. It is concluded from these results that, if p-21.5kDaMBP and ADAM9 are bound, ADAM9 will show α-secretase activity and the generation of sAPPα will be promoted.

Moreover, it was found that, when oligodendrocyte precursor cells were cultivated by using a culture liquid containing only α-GPC, a culture liquid containing only hesperidin and/or narirutin, or a culture liquid containing α-GPC as well as hesperidin and/or narirutin, the proliferation and differentiation of oligodendrocyte precursor cells became remarkable when the culture liquid containing α-GPC as well as hesperidin and/or narirutin was used. This means that ENPP6 shown in nonpatent document 5 is activated by hesperidin and/or narirutin, and α-GPC is rapidly metabolized into choline by the activated ENPP6 and utilized for the differentiation and maturation of oligodendrocyte. This action is heretofore unknown. Based on this, rapid progress of remyelination and recovery from demyelination can be expected by the simultaneous use of α-GPC and hesperidin and/or narirutin.

It was also found that, when drink in which hesperidin and narirutin and α-GPC were added to water, drink in which hesperidin and narirutin were added to water, or drink in which α-GPC was added to water was given to aged TG 2576 mice of 26 months, the expression amount of p-21.5kDaMBP remarkably increased in the brain of the aged mice to which the drink containing hesperidin and narirutin and α-GPC was given compared with in the brain of the aged mice to which the drink containing hesperidin and narirutin was given and in the brain of the aged mice to which the drink containing α-GPC was given. This remarkably increased expression amount was even more remarkable than the total expression amount increased by the administration of the drink containing hesperidin and narirutin and by the administration of the drink containing α-GPC, and therefore, the synergistic effect of hesperidin and/or narirutin and α-GPC was recognized. Moreover, due to this remarkable increase of the expression amount of p-21.5kDaMBP in the brain of the aged mice to which the drink containing hesperidin and narirutin and α-GPC was given, demyelination was recovered by remarkably promoted remyelination as expected by the abovementioned result in the vitro experiment, and in addition, the remarkably increased p-21.5kDaMBP and ADAM9 were bound and α-secretase activity was promoted, the generation of sAPPα in the non-Aβ generation pathway was remarkably promoted.

Furthermore, it was also found that, in the brain of the aged mice to which the drink containing hesperidin and narirutin and α-GPC was given, the expression amount of BACE1, a type of β-secretase, was remarkably decreased compared with in the brain of the aged mice to which the drink containing hesperidin and narirutin was given and in the brain of the aged mice to which the drink containing α-GPC was given, and accordingly, the expression amount of toxic soluble Aβoligomers was remarkably decreased. The expression amount of these remarkably decreased BACE1 and soluble Aβ oligomers was more remarkable than the total amount of the decreased expression amount due to the administration of the drink containing hesperidin and narirutin and the decreased expression amount due to the administration of the drink containing α-GPC. It is conceivable that the expression amount of BACE1 is decreased remarkably and the expression amount of soluble Aβ oligomers is also decreased remarkably because remyelination proceeds promptly and brain damage is recovered by the synergetic effect of α-GPC and hesperidin and/or narirutin.

Therefore, the present invention relates to a composition for treatment and/or prevention of Alzheimer's disease comprising:

at least one kind of compound selected from a group consisting of glycerophosphocholine and pharmacologically permissive salts thereof as a first active ingredient; and at least one kind of compound selected from a group consisting of hesperidin, narirutin and pharmacologically permissive salts thereof as a second active ingredient, which promotes remyelination, promotes the activity of α-secretase, and represses the expression of β-secretase.

The composition for the treatment and/or prevention of Alzheimer's disease of the present invention can substantially reduce the administration amount per day of α-GPC, for which harmful adverse drug reactions have been reported in, for example, nonpatent document 6 by the synergistic effect of α-GPC and hesperidin and/or narirutin. The composition for the treatment and/or prevention of Alzheimer's disease of the present invention preferably comprises 10 to 120 mg of the first active ingredient and 30 to 100 mg of the second active ingredient as a daily dosage for an adult. The daily amount to use the 10 to 120 mg of α-GPC is one-eighth or less of the initial amount of use and one third or less of the later amount of use in nonpatent document 6, and one tenth or less of the amount of use in nonpatent document 7.

In the composition for the treatment and/or prevention of Alzheimer's disease of the present invention, it is preferable to comprise both hesperidin and narirutin as the second active ingredient. Hesperidin and narirutin can be separately combined with α-GPC, and hesperidin and narirutin can be added in the form of Chinpi derived from Citrus unshiu or the extract of the Chinpi. The Chinpi derived from Citrus unshiu abundantly comprises both hesperidin and narirutin, with which both can be added easily and conveniently.

When the composition for the treatment and/or prevention of Alzheimer's disease of the present invention is formulated, the formulation can be a combination drug comprising both the first active ingredient and the second active ingredient, or a kit composed of an agent comprising the first active ingredient and an agent comprising the second active ingredient. The combination drug or each agent constituting the kit may comprise a component other than the first active ingredient and the second active ingredient as far as it does not give an adverse effect to the effect of the present invention. If the composition is in the form of a kit, there is no limitation in the order of administration, and any agent may be administered first.

The composition for the treatment and/or prevention of Alzheimer's disease of the present invention may be administered in the form of either oral or parenteral intake, and may be administered in the form of drug, quasi-drug, health food (including supplement), and so on. The composition for the treatment and/or prevention of Alzheimer's disease of the present invention can be continuously administered as there is no concern about harmful adverse drug reactions, and for the sake of ease, it is preferable to be administered orally as health food.

Advantageous Effects of the Invention

In the present invention, the expression amount of p-21.5kDaMBP remarkably increases due to the synergistic effect of the first active ingredient and the second active ingredient, and due to this remarkable increase, remyelination is remarkably promoted and demyelination is recovered, the α-secretase activity is promoted and the generation of sAPPα is remarkably promoted, and moreover, the expression amount of β-secretase is reduced in accordance with the recovery from demyelination and the generation of Aβ is remarkably repressed. Therefore, the effective treatment and/or prevention of Alzheimer's disease will be accomplished.

DETAILED DESCRIPTION OF THE INVENTION

Figure 1:
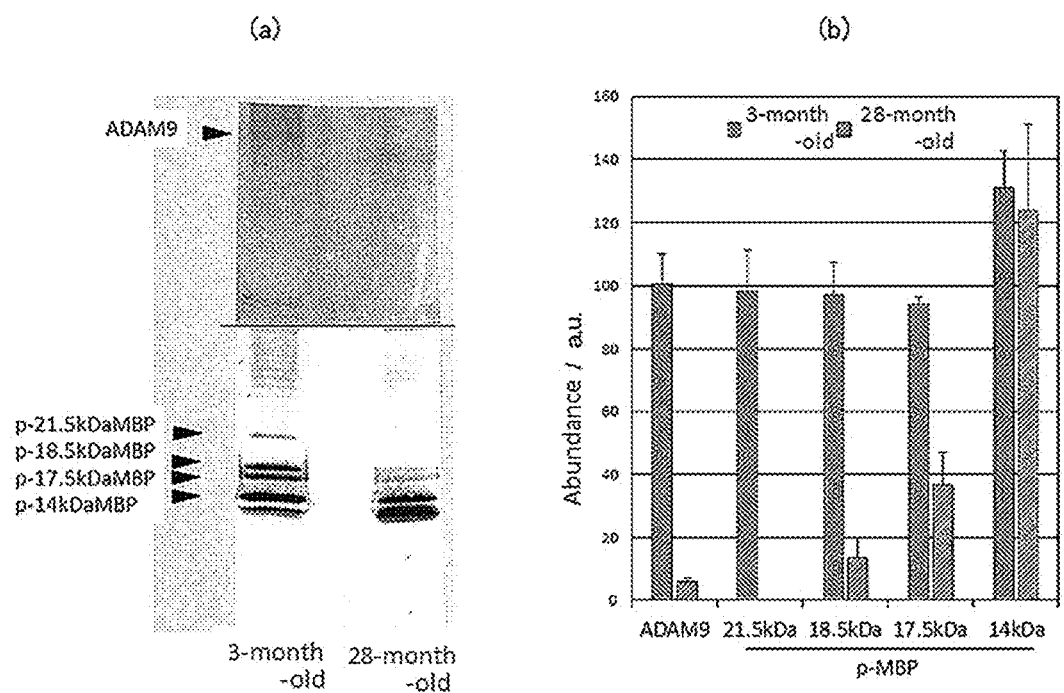
FIG. 1 shows the survey findings of the expression of p-MBP and ADAM9 in the brain of the pathological mouse model of Alzheimer's disease; (a) shows the detection result of p-MBP and ADAM9 by immunoblotting, and (b) shows the abundances of p-MBP and ADAM9.

The composition for the treatment and/or prevention of Alzheimer's disease of the present invention comprises:

at least one kind of compound selected from a group consisting of glycerophosphocholine and pharmacologically permissive salts thereof as a first active ingredient; and at least one kind of compound selected from a group consisting of hesperidin, narirutin and pharmacologically permissive salts thereof as a second active ingredient. By using the first active ingredient and the second active ingredient concurrently, the expression amount of p-21.5kDaMBP remarkably increases compared with when only the first active ingredient is used or only the second active ingredient is used. This remarkably increased expression amount is even more remarkable than the total expression amount increased by the use of the first active ingredient and by the use of the second active ingredient. Moreover, by this remarkable increase of the expression amount of p-21.5kDaMBP, remyelination is remarkably promoted and demyelination is recovered, and in addition, the remarkably increased p-21.5kDaMB and ADAM9 are bound, the α-secretase activity is promoted, and the generation of sAPPα in the non-Aβ generation pathway is remarkably promoted. Also, the expression of β-secretase is repressed in accordance with the recovery of demyelination and the generation of Aβ in the Aβ generation pathway is remarkably repressed.

The α-GPC, the first active ingredient, can be synthesized, for example, by the hydrolysis of phosphatidyl Choline obtained by the oil expression and refining of soy bean with lipase, but commercially available α-GPC can be also used. The α-GPC can be used in the form of a pharmacologically permissive salt, for example, hydrochloride salt, phosphoric salt, citric salt, acetate salt or carbonate, or in the form of a solvate state. Hesperidin and narirutin, the second active ingredient, are also commercially available, which can be used in the form of a pharmacologically permissive salt, for example, hydrochloride salt, phosphoric salt, citric salt, acetate salt or carbonate, or in the form of a solvate state, or further, in the form of a transglycosylation product to improve water solubility. The transglycosylation product is hydrolyzed into hesperidin or narirutin in the body. Also, Chinpi derived from Citrus unshiu that comprises hesperidin and narirutin as active ingredients or an extract obtained by giving extraction treatment such as hot water extract to the Chinpi can also be used. The dried matter of hot water extract liquid is commercially available as solid extract, so it is convenient to use the solid extract. A dry substance of citrus fruit other than Citrus unshiu or an extract thereof can also be used.

In the composition for the treatment and/or prevention of Alzheimer's disease of the present invention, the first active ingredient and the second active ingredient can be combined at desired quantities, and these can be administered by either oral or parenteral intake, and can be administered in the form of drug, quasi-drug, health food (including supplement) and so on. The composition for the treatment and/or prevention of Alzheimer's disease of the present invention does not have harmful adverse drug reactions, so it can be administered continuously, and in terms of convenience, it is preferable to administered by oral intake as a supplement.

The formulation can be a combination drug comprising the first active ingredient and the second active ingredient, or a kit composed of an agent comprising the first active ingredient and an agent comprising the second active ingredient. If the formulation is in the form of a kit, there is no limitation in the order of administration, and any agent may be administered first, and also each may be administered continuously or may be administered after a good period of time.

In case of the combination drug or in case of the agent constituting the kit, it can be formulated for oral use such as capsule, chewable agent, tablet, powder, granule, syrup pharmaceuticals, or a parenteral formulation such as injection, drop or suppository in accordance with the intended purpose. In case of the kit, the form of each agent may be the same or different.

In manufacturing these formulations, the first active ingredient and the second active ingredient are normally mixed with a pharmacologically acceptable vehicle that is selected in accordance with the intended purpose, that is, a solid vehicle such as dextrin and lactose, or a liquid vehicle such as water, saline water or glycerin, and then formulated into a prescribed form. These formulations may comprise other components, for example, vitamins such as vitamin C and vitamin E, minerals such as iron and zinc, functional components such as Gingko leaf extract and docosahexaenoic acid, as well as commonly used additives such as binder, thickener, lubricant, flavor, sweetener, buffer, preservative or antimicrobial agent, as far as an adverse effect to the effect of the present invention is not given.

Further, the composition for the treatment and/or prevention of Alzheimer's disease of the present invention may be blended into various types of food and drink, for example, drinks such as mineral water and refreshing drink, dairy products such as cheese and yogurt, and sweet foods such as jelly, biscuit and candy.

The administration amount of the composition for the treatment and/or prevention of Alzheimer's disease of the present invention may be suitably determined in accordance with the symptoms, age, weight etc., of Alzheimer patients, as well as an administration form or number and the simultaneous use of other formulations, etc., but as the administration amount per day per adult, the combination of 10 to 120 mg of the first active ingredient and 30 to 100 mg of the second active ingredient is generally preferable. If both hesperidin and narirutin are used as the second active ingredient, the combination of 10 to 120 mg of α-GPC, 20 to 75 mg of hesperidin, and 4 to 35 mg of narirutin is preferable. In the present invention, a sufficient improving effect is expected with even such a small amount of administration, and harmful adverse drug reactions is avoided.

The composition for the treatment and/or prevention of Alzheimer's disease of the present invention promotes remyelination, promotes the activity of α-secretase, and represses the expression of β-secretase, so the prompt treatment and/or prevention effect of Alzheimer's disease can be expected. Further, it can be effectively utilized for the treatment and/or prevention of demyelination disease such as multiple sclerosis, mild cognitive disorder, dementia other than Alzheimer's disease, schizophrenia, acute disseminated encephalomyelitis, inflammatory diffuse sclerosis, and Leigh's acute or subacute necrotizing encephalomyelopathy, because it promotes remyelination.

EXAMPLES

The following examples are the explanation of the present invention, but the present invention is not limited to the following examples.

(A) Animal and Breeding Environment

The gene modified Tg2576 mice which Swedish mutant human APP ($APP_{K670N/M671L}$) genes were introduced to were obtained from the Jackson Laboratory in the United States and used in the following experiments. It has been known that Aβ is massively accumulated due to excessive manifestation of APP in the brain of these mice when they are 9 months old or older, and demyelination due to aging occurs when they are 24 months old or older. The Tg2576 mice obtained were kept in breeding facilities at room temperature 25±1 degrees centigrade, relative humidity 55±1% and an illumination cycle of 12 hours light and 12 hours dark (light on: 7:00, light off: 19:00). These animal experiments were conducted in animal experiment facilities of Keio University in accordance with its animal experiment guideline, which was prepared based on the NIH guidelines stipulating the adequate usage and management of experiment animals.

(B) Experiment 1: Relationship Between p-MBP and ADAM9

Nonpatent document 4 shows that sAPPα did not express in the brain of a shiverer mouse with myelin hypoplasia because the non-Aβ generation pathway is inhibited, but the details are unknown; therefore, the relationship between ADAM9, which is known to show α-secretase activity, and p-MBP was investigated with the following experiment through the combination of an immunoprecipitation method using anti-MBP monoclonal antibody and immunoblotting using anti-MBP monoclonal antibody or anti-ADAM9 polyclonal antibody.

(1) Experiment Procedure (a) Brain Solubilization with a Surface-Active Agent

Each of Tg2576 mice of 3 months with little accumulation of Aβ and without demyelination in their brain and Tg2576 mice of 28 months with a large amount of accumulation of Aβ3 and demyelination in their brain was euthanized under inhalation anesthesia using isoflurane (Wako Pure Chemical Industries), and craniotomy was immediately performed to isolate the entire brain. The weight of the isolated brain was measured, and 10 mL of ice-cold phosphate buffered salts (PBS) per gram of brain weight was added, and further 10 mL of a liquid in which 1% concentration of poly(oxyethylene) octylphenyl ether (trade name: Triton (registered trademark) X-100, Sigma-Aldrich Japan) was added to the 100-times diluted solution of 100× Protease Inhibitor Cocktail (Merck) was added, and the brain was solubilized with a homogenizer. The brain homogenate suspension obtained was retrieved to 1.5 mL of an Eppendorf tube and was centrifuged for 30 minutes under the condition of 4 degrees centigrade and 100,000 rpm.

(b) Immunoprecipitation Method

200 μL of the anti-MBP monoclonal antibody SMI-99 (Merck Millipore) with a concentration of 200 μg/mL was added to 200 μL of the supernatant obtained after the centrifugation (protein concentration 1 mg/tube) obtained in the step (a) and allowed to react overnight at 4 degrees centigrade with stirring to form an antigen-antibody complex. Furthermore, 50 μL of Sepharose beads on which Protein A was immobilized (trade name; Protein A-Sepharose (registered trademark): Sigma-Aldrich Japan) was added and reacted at 4 degrees centigrade with stirring overnight to adsorb the antigen-antibody complex on the beads. Next, the obtained suspension was centrifuged at 4 degrees centigrade and 12,000 rpm for 15 minutes. After discarding the supernatant, 800 μL of washing solution (10 mM Tris-HCl (pH 7.4), 150 mM NaCl, 0.005% polyoxyethylene sorbitan monolaurate (trade name: Tween-20): all Sigma-Aldrich Japan) was added to the sediment, slowly pipetted, and then centrifuged at 4 degrees centigrade, 12,000 rpm for 15 minutes. After repeating the above procedure from addition of washing solution to centrifugation twice more, 50 μL of 2× sodium dodecyl sulfate (SDS) sample buffer (0.125 M Tris-HCl (pH 6.8) (Wako Pure Chemical Industries), 20% Glycerol (Wako Pure Chemical Industries), 4% SDS (Wako Pure Chemical Industries), 10% 2-mercaptoethanol (Nacalai Tesque), 0.004% Bromophenol Blue (Sigma-Aldrich Japan)) was added to the sediment, heated at 100 degrees centigrade for 5 minutes, and then centrifuged at 4 degrees centigrade and 14,000 rpm for 15 minutes to obtain a supernatant fluid containing the antigen-antibody complex.

(c) Electrophoresis (SDS-PAGE)

SDS-PAGE was conducted by using 4 to 20% gradient gel (TEFCO). The gel board was set in an electrophoresis apparatus and electrophoresis buffer was introduced. Then 25 μL of the supernatant fluid containing the antigen-antibody complex obtained in the abovementioned process (b) was introduced into wells of the gel board, was electrophoresed at room temperature for about 30 minutes under the condition of 5 mA, and was further electrophoresed for about 90 minutes under the condition of 25 mA.

(d) Immunoblotting

Polyvinylidene difluoride (PVDF) membrane (trade name: Immobilon-P: pore size 0.45 μm, Merck Millipore) was introduced to a transcription liquid (31 mM Tris (Nacalai Tesque), 0.24M Glycine (Sigma-Aldrich Japan), 20% Methanol (Wako Pure Chemical Industries)) and shaken for 15 minutes. The PVDF membrane retrieved and the gel after electrophoresis obtained in the abovementioned process (c) were made into contact, an electric current was passed at room temperature under the condition of 20 mA/cm$^2$, and protein was transcribed to the PVDF membrane. After the transcription and staining with Coomassie Brilliant Blue (Wako Pure Chemical Industries) and drying, blocking treatment was given at a room temperature for 1 hour to the PVDF membrane by using a blocking buffer in which 5% skim milk (Defco) was dissolved into 10-fold diluted 10× Tris Buffered Saline (TBS) (0.5M Tris (pH 8.1) (Nacalai Tesque), 1.5M NaCl (Sigma-Aldrich Japan), 1N hydrochloric acid (Wako Pure Chemical Industries)).

A primary antibody response was given at 4 degrees centigrade for all night long to the PVDF membrane obtained after the blocking treatment by using Anti-p-MBP monoclonal antibody PC12 (Merck Millipore, 1/500 dilution) or Anti-ADAM9 polyclonal antibody C-15 (Santa Cruz Biotechnology, 1/500 dilution) together with Mouse monoclonal antibody against β-actin as an internal control (Sigma-Aldrich Japan, 1/1000 dilution) as primary antibodies. The abovementioned blocking buffer was used for dilution. The PVDF membrane after the primary antibody response was cleansed 3 times with a blocking buffer in which 1% skim milk was dissolved into 10-fold diluted 10×TBS. Then, a secondary antibody response was conducted at room temperature for 2 hours by using Alkaline Phosphatase-conjugated Affinipure Goat Anti-Mouse IgG (H+L) (Jackson ImmunoResearch Laboratories) or Alkaline Phosphatase-conjugated Affinipure Goat Anti-Rabbit IgG (H+L) (Jackson ImmunoResearch Laboratories), which were diluted 800 to 1000 times with the blocking buffer, the PVDF membrane was cleansed 3 times for 10 minutes each time by using a blocking buffer in which 1% skim milk was dissolved into 10-fold diluted 10×TBS, and antigen was detected by an alkaline phosphatase reaction. The alkaline phosphatase reaction was conducted by reacting for 30 minutes to 1 hour in a shaded condition by using 5-bromo-4-chloro-3-indolylphosphate (Wako Pure Chemical Industries) as a substrate for alkaline phosphatase, nitro blue tetrazolium (Wako Pure Chemical Industries) as a color coupler, and a buffer solution (0.1M Tris (Nacalai Tesque), 0.1M NaCl (Sigma-Aldrich Japan), 0.05M MgCl$_2$ (Sigma-Aldrich Japan)). The detection result of antigen was determined with the mean value±standard error of 3 independent experiments.

(2) Experimental Result

FIG. 1 shows the survey findings of the abundances of p-MBP and ADAM9 in the brains of the Tg2576 mice of 3 months and the Tg2576 mice of 28 months through the abovementioned processes (a) to (d). FIG. 1(a) shows the image of the PVDF membrane in which p-MBP and ADAM9 are detected by the alkaline phosphatase reaction, and FIG. 1(b) shows the abundances of p-MBP and ADAM9 obtained by the image of FIG. 1(a), which are normalized by β-actin as the internal standard.

Tg2576 mice have 4 MBP isoforms, with molecular masses 14 kDa, 17.5 kDa, 18.5 kDa and 21.5 kDa. FIG. 1(b) shows that all these 4 isoforms are expressed in the brain of the Tg2576 mice of 3 months old, while in the brain of the Tg2576 mice of 28 months old, higher molecular mass isoforms are expressed less and p-21.5kDaMBP is not expressed at all. Also, it is shown that, compared with the abundance of ADAM9 detected in the experiment using the brain of the Tg2576 mice of 3 months old, the abundance of ADAM9 detected in the experiment using the brain of the Tg2576 mice of 28 months old is remarkably low, and ADAM9 is scarcely detected. It is found from these results that p-MBP, especially p-21.5kDaMBP is bound to ADAM 9 in the brain of Tg2576 mice. As it is known that enzyme activity is controlled by the binding of adaptor protein to the cytoplasm domain of ADAM9, so it is considered that the binding of p-MBP, especially p-21.5kDaMBP to the cytoplasm domain of ADAM9 causes ADAM9 to transform into a mature form that shows α-secretase activity, and the generation of sAPPα is promoted.

(C) Experiment 2: In Vitro Confirmation of the Combination Effect of α-GPC and Hesperidin/Narirutin The cerebrum of mice of the 18th fetal day was enzymatically dispersed with a mixed solution of 0.3% of Dispase II and 0.05% of Deoxyribonuclease (both from Roche Molecular Biochemicals) deluted by Dulbecco's Modified Eagle's Medium (DMEM, Invitrogen), the dispersed cells obtained were cleansed with DMEM, and the dissociated cells were put through nyron mesh with pore diameter 70 μm. Then, the cells were suspended in DMEM containing 10% of bovine fetal serum, disseminated on poly-L-ricin coated culture dishes (diameter: 10 cm) at the cell density of 2.0×10$^7$ per dish and cultivated for 5 days. Next, the cells after cultivation were exfoliated by using PBS containing 0.2% of trypsin, centrifuged for 10 minutes under the condition of 4 degrees centigrade and 1,000 rpm, and the sediment was suspended in 10 mL of a serum-free culture medium (a medium in which glucose (5.6 mg/ml), kanamycin (60 mg/ml), insulin (5 μg/ml), transferrin (0.5 μg/ml), BSA (100 μg/ml), progesterone (0.06 ng/ml), putrescine (16 μg/ml), sodium selenite (40 ng/ml), thyroxine (T4) (40 ng/ml) and triiodothyronine (T3) (30 ng/ml) were added to DMEM) at the cell density of 2.5×10$^6$ per 1 mL, cultivated at 37 degrees centigrade for two hours in a CO$_2$ incubator, and oligodendrocyte precursor cells (OPCs) were obtained.

Then, the OPCs obtained were disseminated on non-coated culture dishes (diameter: 10 cm) to which the abovementioned serum-free culture medium was introduced at the cell density of 2.5×10$^6$ per dish, and any one of PBS alone (control), PBS containing hesperidin (H), PBS containing narirutin (N), PBS containing hesperidin and narirutin, PBS containing α-GPC (G), or PBS containing hesperidin and narirutin and α-GPC was added, and the OPCs obtained were cultivated for 48 hours. The amounts of hesperidin, narirutin and α-GPC in the culture medium were adjusted so that the final concentration of each was 10 μM.

Figure 2:
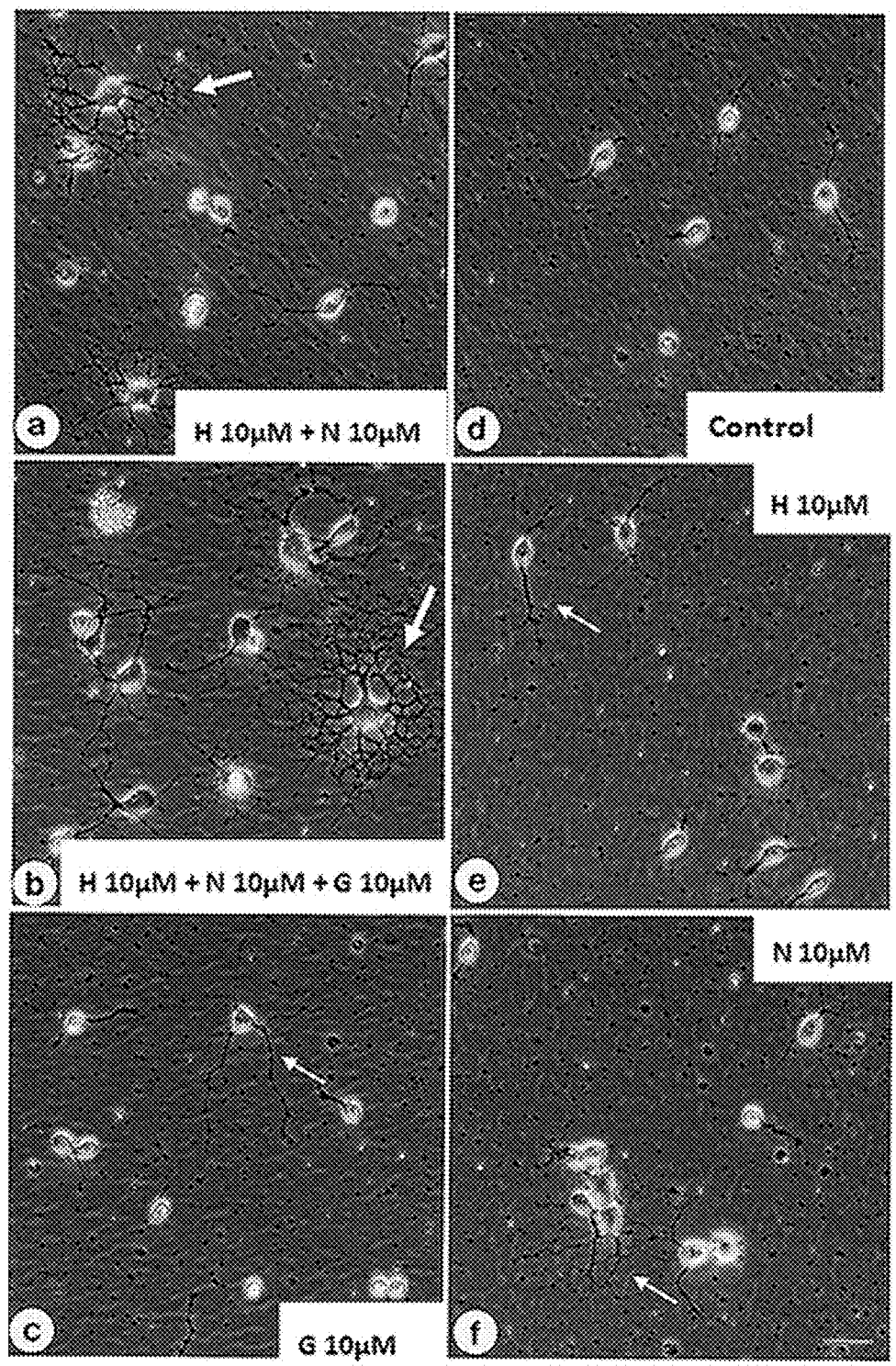
FIG. 2 shows phase-contrast photos at 400-fold magnification showing the state of proliferation and differentiation of oligodendrocyte precursor cells when oligodendrocyte precursor cells are cultivated in a culture vessel containing α-GPC, hesperidin, narirutin or a combination thereof.

FIG. 2 shows the phase-contrast photos at 400-fold magnification of cells after 48 hours are elapsed. In case of cultivation in the medium containing 10 μM of hesperidin, 10 μM of narirutin or 10 μM of α-GPC, the number of cells increases and protrusions indicated by allows are generated, which indicates that the proliferation and differentiation of OPCs proceeds, compared with the control. Also, in case of cultivation in the medium containing 10 μM of hesperidin and 10 μM of narirutin, the proliferation and differentiation of OPCs are accelerated. This effect is considered to be given by the use of a medium containing a total density of 20 μM of the second active ingredient (hesperidin/narirutin). Further, in case of cultivation in the medium containing 10 μM of hesperidin, 10 μM of narirutin and 10 μM of α-GPC, the differentiation and maturation of OPCs are remarkably accelerated as indicated by allow. This shows that ENPP6 is activated by hesperidin and/or narirutin, α-GPC is promptly metabolized into choline by the activated ENPP6 and utilized by the differentiation and maturation of oligodendrocytes.

To further confirm the combination effect, the abovementioned OPCs were disseminated on non-coated culture dishes (diameter: 10 cm) to which the abovementioned serum-free culture medium was introduced at the cell density of $2.5 \times 10^6$ per dish, and any one of PBS alone (control), PBS containing α-GPC or PBC containing α-GPC and hesperidin was added and cultivated for 48 hours. The amounts of hesperidin and α-GPC were adjusted so that the final concentration of each was 0.1 mM or 1 mM. Moreover, the OPCs were immunostained with O1 antibody as a differentiation marker of oligodendrocytes, the number of total cells and the number of O1 positive oligodendrocytes in a single field of view under the microscope were counted respectively, and the ratio of the number of O1 positive oligodendrocytes against the number of total cells were calculated. The results are shown in FIG. 3.

Figure 3:
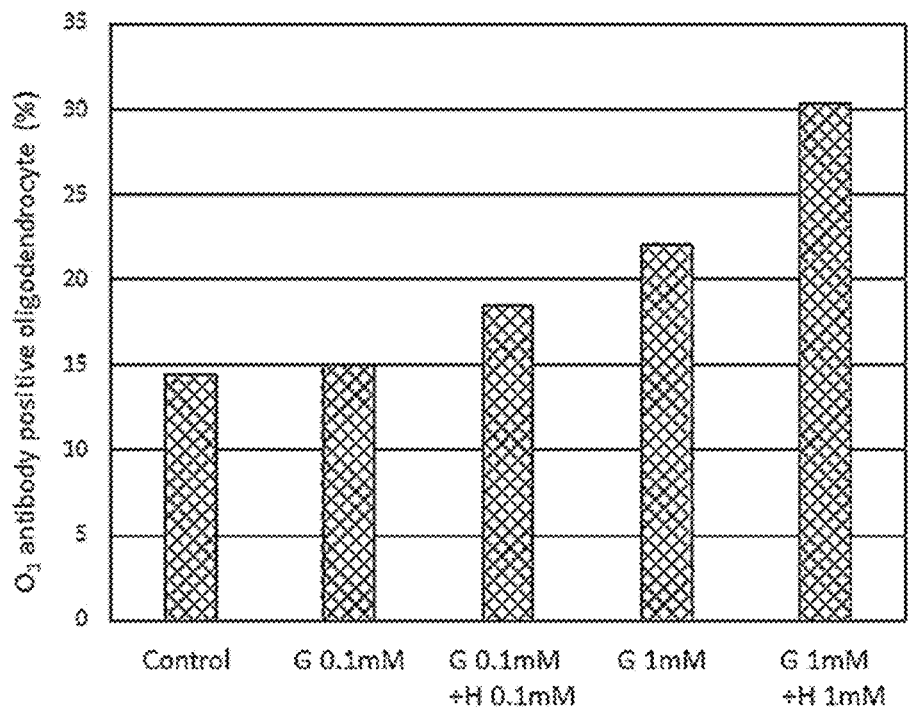
FIG. 3 shows the results of an experiment in which oligodendrocyte precursor cells are cultivated in a culture fluid containing α-GPC or in a culture fluid containing α-GPC and hesperidin, and then immunostaining is conducted by using the O1 antibody as a differentiation marker for oligodendrocyte, and the ratio of the number of O1 positive oligodendrocytes against the total number of cells is calculated.

) As is understood by FIG. 3, O1 positive oligodendrocytes hardly increases compared with the control if OPCs are cultivated by using the medium containing 0.1 mM of α-GPC, but by adding 0.1 mM of hesperidin to the medium, the ratio of O1 positive oligodendrocytes sharply increases, even exceeding the half of the amount of increase in case of the cultivation using the culture medium containing 1 mM of α-GPC. In case where 1 mM of hesperidin is added to the culture medium containing 1 mM of α-GPC, O1 positive oligodendrocytes remarkably increases, too. Therefore, it is confirmed that the simultaneous use of α-GPC and hesperidin and/or narirutin can rapidly make OPCs differentiate and mature into oligodendrocytes. Based on these results, it is expected that remyelination will rapidly proceed and demyelination will be recovered with the simultaneous use of α-GPC and hesperidin and/or narirutin.

(D) Experiment 3: Relationship of the Administration of α-GPC/Chinpi and the Expression Amount of p-21.5kDaMBP/Mature ADAM9/sAPPα/CTF-α/BACE1/Aβ Oligomers Based on the abovementioned result of Experiment 1, it is expected that the α-secretase activity of ADAM9 is promoted and therefore, the generation of sAPPα in the non-Aβ generation pathway is promoted, the generation of Aβ in the Aβ generation pathway is repressed and therefore the generation of toxic soluble Aβ oligomers is repressed if the expression amount of p-21.5kDaMBP is increased. Therefore, the relationship between the administration of α-GPC/Chinpi and the expression amount of p-21.5kDaMBP/mature ADAMS/sAPPα/CTF-α/BACE1/Aβ oligomers was surveyed.

(1) Experiment Procedure (Aa) Administration of α-GPC/Chinpi

With the solid extract of Chinpi (containing 20.8 mg of hesperidin and 3.38 mg of narirutin per gram: UCHIDA WAKANYAKU Ltd.) and a powder containing 85% of α-GPC (NOF GPC85R: NOF Corporation), GHN drink in which 0.017 w/v % of α-GPC and 0.5 w/v % of the solid extract of Chinpi (hesperidin: 0.0104 w/v %, narirutin: 0.0017 w/v %) were dissolved into distilled water (Example), HN drink in which 0.5 w/v % of the solid extract of Chinpi was dissolved into distilled water (Comparative Example 1) and G drink in which 0.017 w/v % of α-GPC was dissolved into distilled water (Comparative Example 2) were prepared. Aged Tg2576 mice of 26 months (average weight: 30 g) were separated into 4 groups, and GHN drink, HN drink, G drink, or water as a control was given to each group for 2 months by free intake (average amount of drinking: 4 mL/day). If the amount of administration of α-GPC, hesperidin and narirutin in this administration experiment is converted to the administration amount of an adult human weighing 50 kg by using a coefficient "10" to convert the species difference between human beings and mice (see Regul. Toxicol. Pharmacol. 24, 108-120), the administration amount of α-GPC is 113.3 mg/day, the administration amount of hesperidin is 69.3 mg/day, and the administration amount of narirutin is 11.3 mg/day. After 2 months of free intake, the mice to which GHN drink was administered, the mice to which HN drink was administered, the mice to which G drink was administered and the control mice were euthanized under inhalation anesthesia using isoflurane (Wako Pure Chemical Industries), craniotomy was immediately performed, and the entire brain was isolated and stored at −80 degrees centigrade until use.

(Bb) Solubilization of Brain with a Surface-Active Agent

The stored brains of the mice to which GHN drink was administered, the mice to which HN drink was administered, the mice to which G drink was administered and the control mice were used to conduct the preparation and centrifugation of brain homogenate suspension in the same procedure as the process (a) of Experiment 1, and after centrifugation, the supernatant fluid was separated as a soluble fraction and the sediment was separately as an insoluble fraction, and both were stored at −80 degrees centigrade.

(Cc) Electrophoresis (SDS-PAGE)

The soluble fraction obtained in the abovementioned process (bb) was diluted 4 times with a 4×SDS sample buffer (0.0625 M Tris-HCl (pH 6.8) (Wako Pure Chemical Industries), 10% Glycerol (Wako Pure Chemical Industries), 2% SDS (Wako Pure Chemical Industries), 5% 2-Mercaptoethanol (Nacalai Tesque), 0.002% Bromophenol blue (Sigma-Aldrich Japan)), left in a constant-temperature bath of 100 degrees centigrade for 10 minutes, and a sample for SDS-PAGE was obtained. SDS-PAGE was carried out by using the sample for SDS-PAGE obtained with the same procedure as shown in the process (c) of Experiment 1.

(dd) Immunoblotting

With the gel after electrophoresis obtained in the abovementioned process (cc), protein was transcribed to the PVDF membrane and blocking treatment before the subsequent primary antibody response was given in the same procedure as shown in the process (d) of Experiment 1. Then, the primary antibody response of the PVDF membrane after the blocking treatment was conducted at 4 degrees centigrade for all night long. The antibodies used were Mouse monoclonal antibody 22C11 that recognizes the N-terminal of APP (Merck Millipore, 1/600 dilution), Mouse monoclonal antibody 6E10 that recognizes $Aβ_{1-16}$ (Covance Inc., 1/1000 dilution), Mouse monoclonal antibody 4G8 that recognizes $Aβ_{17-24}$ (Covance Inc., 1/500 dilution), an antibody that recognizes the C-terminal of BACE1 (Calbiochem Inc., 1/500 dilution), an antibody that recognizes the metallopeptidase domain of ADAMS (Bethyl Laboratories Inc., 1/500 dilution), Mouse monoclonal antibody against β-actin as an internal standard (Sigma-Aldrich Japan, 1/1000 dilution) and Anti-p-MBP monoclonal antibody PC12 (Merck Millipore, 1/500 dilution each). To dilute each antibody, a blocking buffer in which 5% of skim milk was dissolved into 10-fold diluted 10×TBS was used. After the primary antibody response, the PVDF membrane was cleansed 3 times for 10 minutes each by using a blocking buffer in which 1% of skim milk was dissolved into 10-fold diluted 10×TBS. Then a second antibody response was conducted at room temperature for 2 hours by using Alkaline Phosphatase-conjugated Affinipure Goat Anti-Mouse IgG (H+L) (Jackson ImmunoResearch Laboratories) which was 800-fold diluted with the blocking buffer, the PVDF membrane was cleansed 3 times for 10 minutes each by using a blocking buffer in which 1% of skim milk was dissolved into 10-fold diluted 10×TBS, and antigen was detected by alkaline phosphatase reaction with the same procedure as shown in the process (d) of Experiment 1. The detection result of antigen was obtained with the mean value±standard error of 3 independent experiments.

(2) Experimental Result

Figure 4:
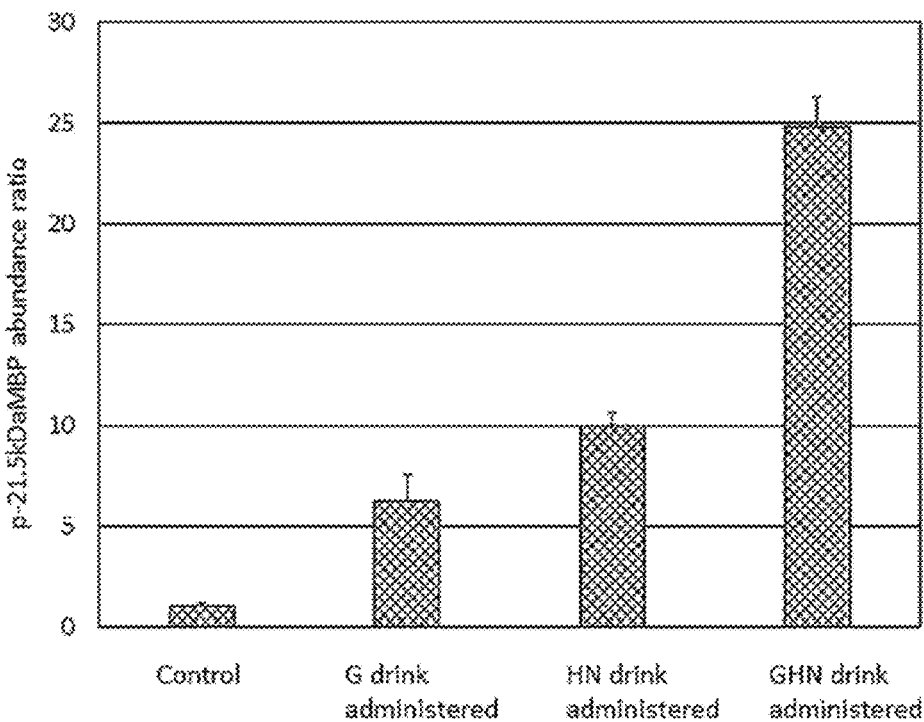
FIG. 4 shows the survey findings of the abundance of p-21.5kDaMBP in the brain of the pathological mouse model of Alzheimer's disease when α-GPC (G drink), the solid extract of Chinpi (HN drink) and both (GHN drink) are administered.

FIG. 4 is a figure in which the abundance of p-21.5kDaMB that is normalized by β-actin as the internal standard is shown in the form of an abundance ratio in which the abundance in the brain of the control mice is set to 1. As can be understood from FIG. 4, the expression amount of p-21.5kDaMBP is increased to approximately 6 times by the administration in G drink (Comparative Example 2), and is increased to approximately 10 times by the administration of HN drink (Comparative Example 1), but the amount increased by the administration of GHN drink (Example) is approximately 25 times and remarkable. In other words, the expression amount increased by the administration of GHN drink is remarkable compared with the total amount of the expression amount increased by the administration of HN drink and the administration of G drink, and the synergism of α-GPC and hesperidin/narirutin is found.

Figure 5:
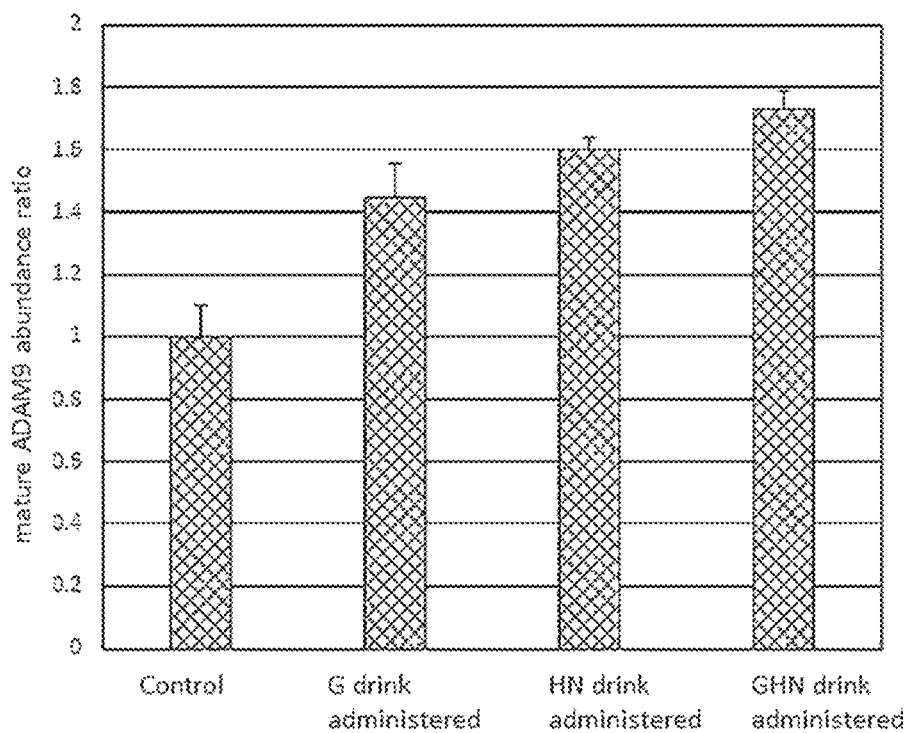
FIG. 5 shows the survey findings of the abundance of mature ADAM9 in the brain of the pathological mouse model of Alzheimer's disease when α-GPC, the solid extract of Chinpi and both are administered.
Figure 6:
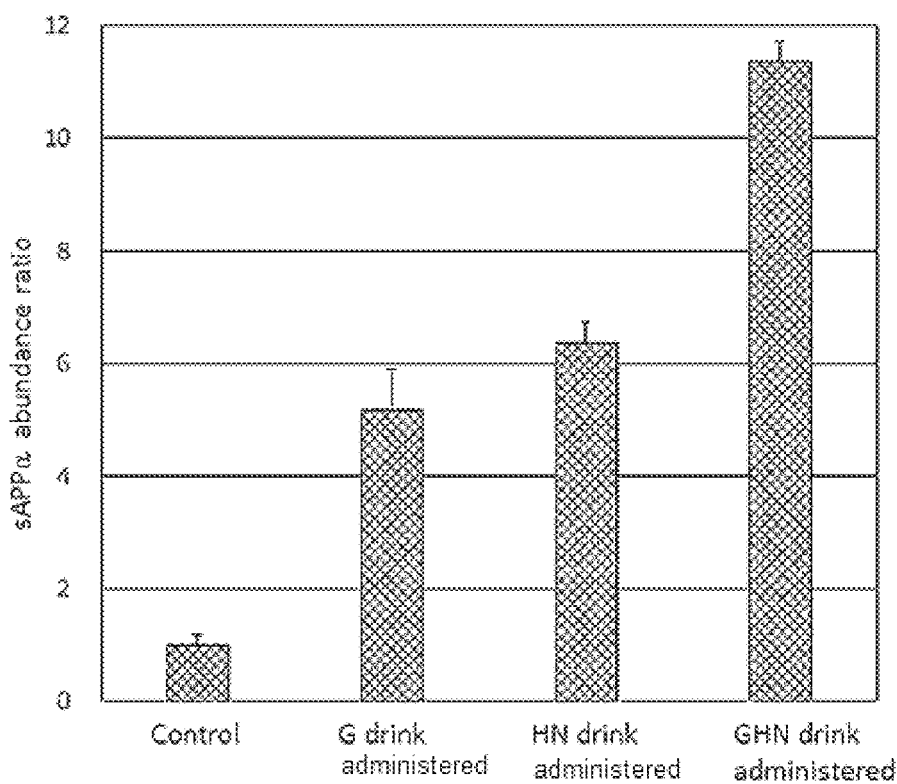
FIG. 6 shows the survey findings of the abundance of sAPPα in the brain of the pathological mouse model of Alzheimer's disease when α-GPC, the solid extract of Chinpi and both are administered.
Figure 7:
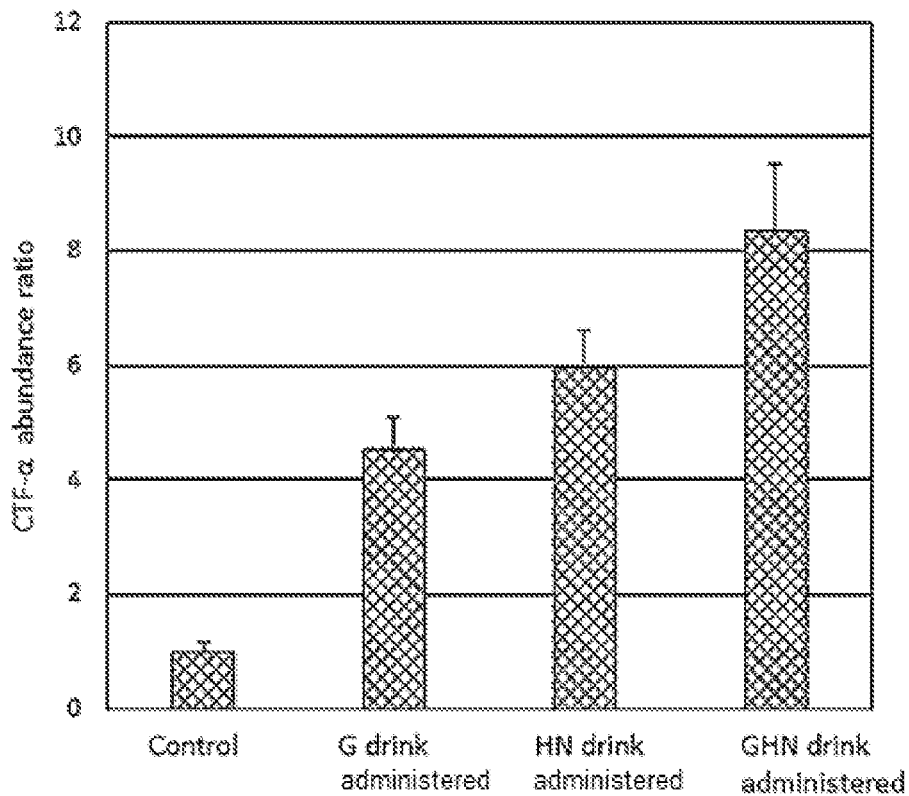
FIG. 7 shows the survey findings of the abundance of CTF-α in the brain of the pathological mouse model of Alzheimer's disease when α-GPC, the solid extract of Chinpi and both are administered.

FIG. 5 is a figure in which the abundance of mature ADAM9 normalized by β-actin as the internal standard is shown in the form of an abundance ratio in which the abundance in the brain of the control mice is set to 1. As can be understood by the result of Experiment 1, if p-MBP, especially p-21.5kDaMBP, is bound to the cytoplasm domain of ADAM9, ADAM9 becomes a mature type that shows α-secretase activity. The expression amount of mature ADAM9 is increased to approximately 1.45 times by the administration of G drink (Comparative Example 2), and is increased to approximately 1.60 times by the administration of HN drink (Comparative Example 1), and is increased to approximately 1.73 times by the administration of GHN drink (Example). This is the result of the remarkable increase of p-MBP, especially p-21.5kDaMBP by the synergistic action of α-GPC and hesperidin/narirutin, as can be understood from FIG. 4. FIG. 6 is a figure in which the abundance of sAPPα normalized by β-actin as the internal standard is shown in the form of an abundance ratio in which the abundance in the brain of the control mice is set to 1, and FIG. 7 is a figure in which the abundance of CTF-α normalized by β-actin as the internal standard is shown in the form of an abundance ratio in which the abundance in the brain of the control mice is set to 1. The sAPPα and CTF-α are generated by α-secretase cleaving APP in the non-Aβ generation pathway. As can be understood in FIG. 6, the expression amount of sAPPα is increased to approximately 5.2 times by the administration of G drink (Comparative Example 2), and is increased to approximately 6.4 times by the administration of HN drink (Comparative Example 1), while the amount increased by the administration of GHN drink (Example) is increased to as much as approximately 11.4 times. Further, as can be understood from FIG. 7, the expression amount of CTF-α is increased to approximately 4.6 times by the administration of G drink (Comparative Example 2), and is increased to approximately 6.0 times by the administration of HN drink (Comparative Example 1), while the amount increased by the administration of GHN drink (Example) is increased to as much as approximately 8.4 times. The expression amount of sAPPα shown in FIG. 6 is well correlated with the expression amount of p-21.5kDaMBP in FIG. 4, which shows the synergic action of α-GPC and hesperidin/narirutin with regard to the acceleration of α-secretase activity. The increase in the expression amount of mature ADAM9 by the simultaneous use of α-GPC and hesperidin/narirutin as shown in FIG. 5 is small, compared with the increase in the expression amount of sAPPα by the simultaneous use of α-GPC and hesperidin/narirutin as shown in FIG. 6 or the increase in the expression amount of CTF-α by the simultaneous use of α-GPC and hesperidin/narirutin as shown in FIG. 7. There are many ADAMs other than ADAM9 that show α-secretase activity (for example, ADAM 10, ADAM 17), and it is conceivable that the expression amount of sAPPα and CTF-α is considerably increased because the expression amount of these entire ADAMs is remarkably increased.

Figure 8:
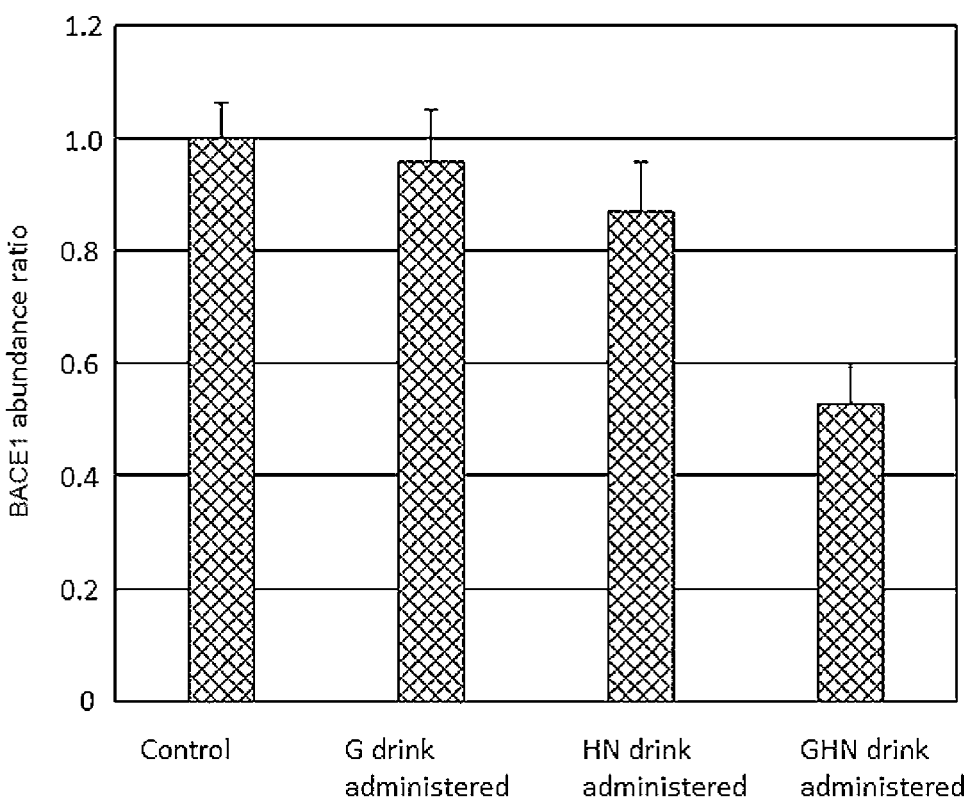
FIG. 8 shows the survey findings of the abundance of BACE1 in the brain of the pathological mouse model of Alzheimer's disease when α-GPC, the solid extract of Chinpi and both are administered.
Figure 9:
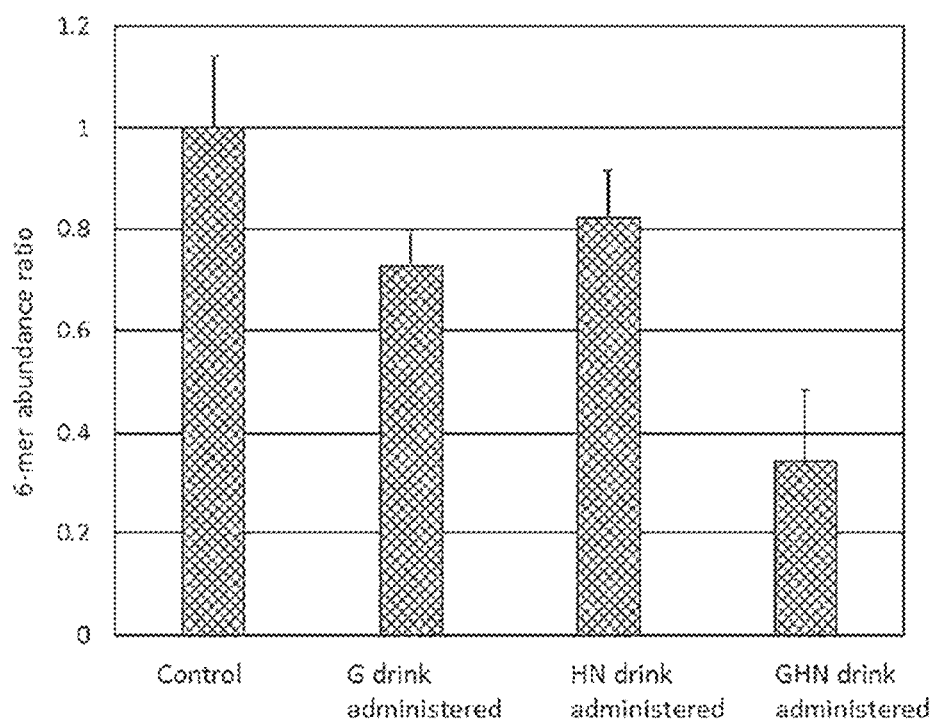
FIG. 9 shows the survey findings of the abundance of Aβ oligomer in the brain of the pathological mouse model of Alzheimer's disease when α-GPC, the solid extract of Chinpi and both are administered.

FIG. 8 is a figure in which the abundance of BACE1 as one kind of β-secretase normalized by β-actin as the internal standard is shown in the form of an abundance ratio in which the abundance in the brain of the control mice is set to 1, and FIG. 9 is a figure in which the abundance of Aβ hexamer (hereinafter referred to as "6-mer") normalized by β-actin as the internal standard is shown in the form of an abundance ratio in which the abundance in the brain of the control mice is set to 1. The 6-mer is an Aβ aggregation core peptide, a kind of soluble Aβ oligomers whose relationship between cognitive dysfunction is strongly suggested, and when the polymerization further proceeds with the core of 6-mer, toxic soluble 12-mer and senile plaque are generated. As can be understood from FIG. 8, the expression amount of BACE1 is just decreased to approximately 0.96 times by the administration of G drink (Comparative Example 2) and is decreased to approximately 0.87 times by the administration of HN drink (Comparative Example 1), but is decreased to as low as approximately 0.53 times by the administration of GHN drink (Example). Further, as can be understood from FIG. 9, the expression amount of 6-mer is just decreased to approximately 0.73 times by the administration of G drink (Comparative Example 2) and is decreased to approximately 0.82 times by the administration of HN drink (Comparative Example 1), but is decreased to as low as approximately 0.34 times by the administration of GHN drink (Example). These results show the synergetic action between α-GPC and hesperidin/narirutin. Especially, the reducing effect of BACE1 by simultaneously using α-GPC and hesperidin/narirutin is remarkable, and this is considered to reflect the recovery from demyelination. In other words, BACE1 is not an enzyme specific to neurons but rather develop aboundingly in astrocytes; it has been found that BACE1 develops in reactive astrocytes of the brain of Alzheimer's patients, and these reactive astrocytes develops when the brain is damaged. As is shown below, remyelination swiftly proceeds and demyelination is recovered by the synergetic effect of α-GPC and hesperidin/narirutin. It is considered that due to the recovery of demyelination, the development of reactive astrocytes is repressed, and accordingly the expression amount of BACE1 remarkably decreases and furthermore, the expression amount of soluble Aβ oligomers is remarkably decreased.

The abovementioned results show that with the composition of the present invention comprising α-GPC and hesperidin/narirutin, these active ingredients act synergistically, the expression amount of p-21.5kDaMBP remarkably increases; the α-secretase activity of ADAMS is promoted due to binding with this remarkably increased p-21.5kDaMBP and the generation of sAPPα and CTF-α is remarkably promoted, and in addition, the development of BACE1 is repressed and the Aβ generation pathway and consequently the generation of soluble Aβ oligomers, of which the relationship with cognitive dysfunction has been strongly suggested, are remarkably repressed. Therefore, the composition of the present invention is remarkably effective for the treatment and/or prevention of Alzheimer's disease.

(E) Experiment 4: Relationship Between the Administration of α-GPC/Chinpi and Remyelination (1) Experiment Procedure The cerebra of the mice to which GHN drink was administered, the mice to which HN drink was administered, the mice to which G drink was administered and the control mice, which were stored in the process (aa) in Experiment 2, were observed with an electron microscope. The cerebrum of each mouse was prefixed with 2% glutaraldehyde and further postfixed with 1% $OsO_4$. The specimens were dehydrated in ethanol, then embedded into epoxy resin (trade name: Quetol 812, Nisshin EM Co., Ltd.), ultra-thin sections dyed with 2% uranyl acetate and a lead solution were obtained, and these were observed with an electron microscope at 19,000-fold magnification. To measure the G-ratio (the ratio of the diameter of an axon to the diameter of the axon and the surrounding myelin sheath: see FIG. 11), at least 3 mice per group were used and 8 to 10 electron micrographs were taken for each mouse, the G-ratios were measured for at least 90 axons, and the average value and standard deviation were calculated.

(2) Experimental Result

Figure 10:
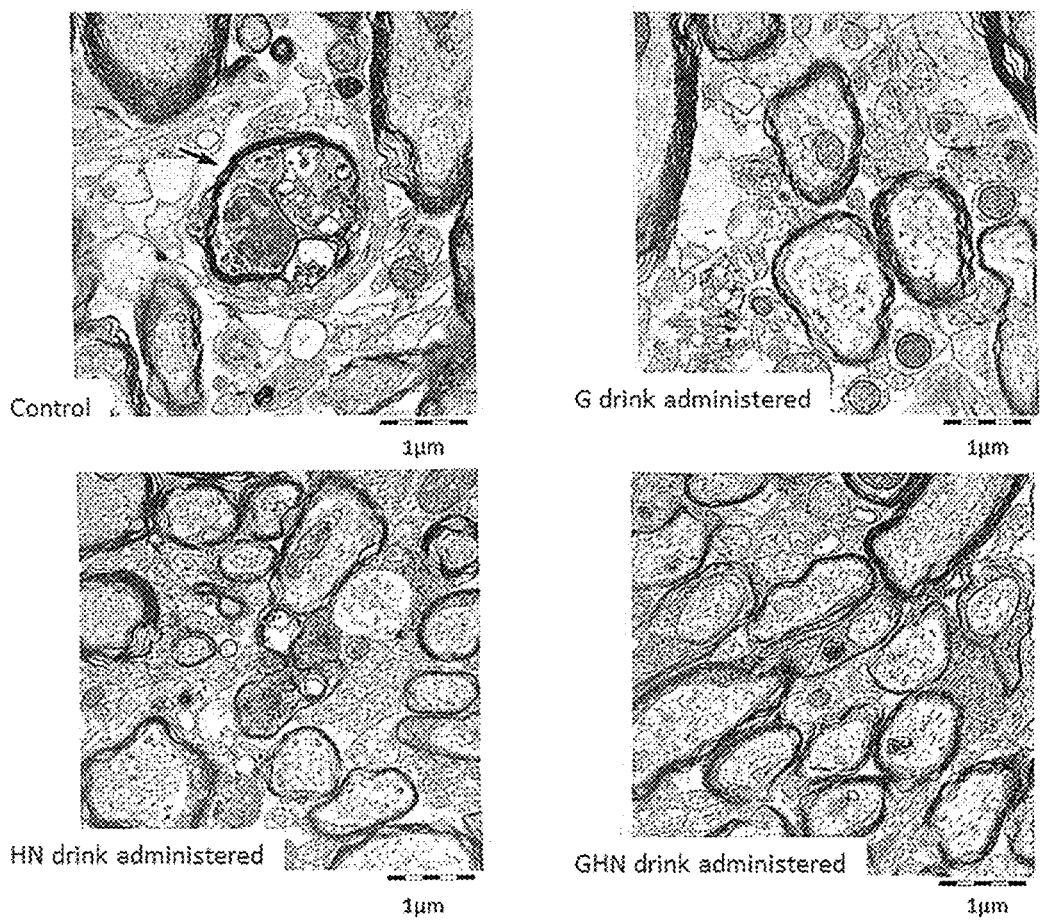
FIG. 10 shows electron micrographs at 19,000-fold magnification that show the recovery from demyelination when α-GPC, the solid extract of Chinpi and both are administered to the pathological mouse model of Alzheimer's disease.
Figure 11:
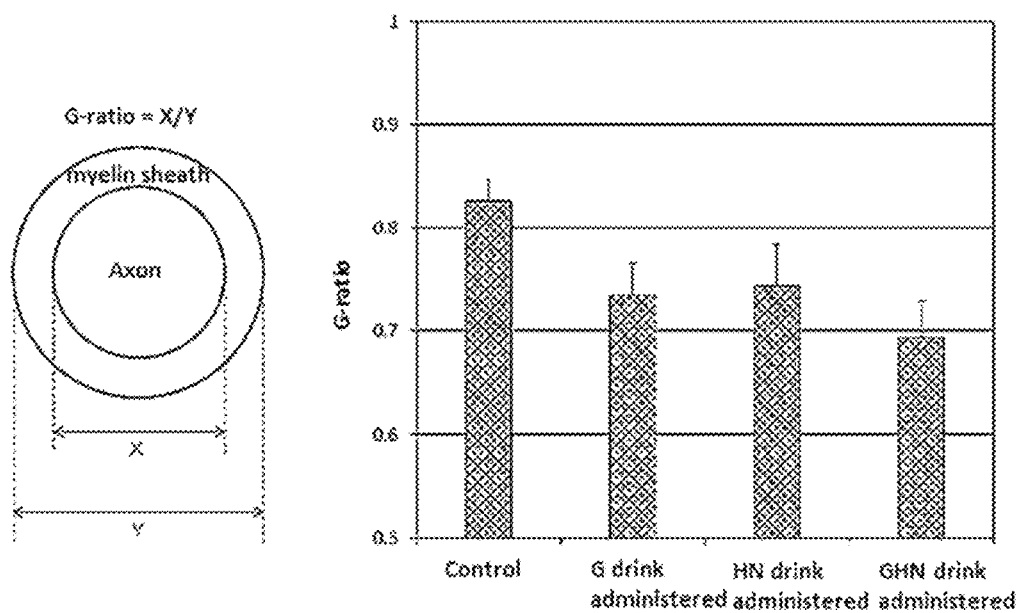
FIG. 11 shows the evaluation results of the recovery from demyelination with G-ratio values when α-GPC, the solid extract of Chinpi and both are administered to the pathological mouse model of Alzheimer's disease.

FIG. 10 shows the electron micrographs of the brain of each mouse. The p-MBP stratifies the myelin membrane around the axon and makes an effect of maintaining the compression of myelin. FIG. 10 shows that, in the brain of the control mice, the compression of the myelin membrane as indicated by an arrow is not sufficient and demyelination is proceeding, while demyelination is recovering as remyelination proceeds due to the administration of G drink (Comparative Example 2) and the administration of HN drink (Comparative Example 1), and that remyelination further proceeds due to the administration of GHN drink (Example) and the recovery from demyelination is remarkably recognized. FIG. 11 shows the value of the G-ratio calculated from the electron micrographs. When myelin membranes are stratified and compressed around the axon, the G-ratio value reduces, so the reduction in the G-ratio value serves as a measure for the recovery from demyelination. As can be understood from FIG. 11, the G-ratio value in the cerebrum of the control mice is approximately 0.83, the G-ratio value in the cerebrum of the mice to which G drink was administered and the mice to which HN drink was administered is approximately 0.74; these values are similar to the G-ratio value obtained by the administration of Ninjin'yoeito in nonpatent document 1, but the G-ratio value in the cerebrum of the mice to which GHN drink was administered is further reduced to approximately 0.69. This is on an equality with the G-ratio value in the cerebrum of normal mice, which represents an extraordinary result. This is considered to cause the remarkable decrease of BACE1, and consequently, the remarkable decrease of soluble Aβ oligomers, as mentioned above.

From the abovementioned results, it is found that, with the composition comprising the α-GPC and hesperidin/narirutin of the present invention, these ingredients act synergistically, remyelination is remarkably promoted and demyelination shows recovery. Therefore, the composition of the present invention is extremely effective for the treatment and/or prevention of Alzheimer's disease.

(F) The Confirmation of Improvement Effect on Cognitive Functions

A sickness tablet containing a total of 70 mg of hesperidin and narirutin as well as 40 mg of α-GPC was fabricated as daily dosage and administered to trialists for 2.5 to 4 months, and their scores of Hasegawa's dementia scale (HDS-R) were evaluated. The HSD-R is evaluated with a maximum score of 30, where dementia is suspected if an examinee scores 20 or less, and in case of definitive diagnosis, scores of 20 or less are assessed as mild, scores of 11 to 19 are assessed as medium, and scores of 10 or less are assessed as advanced. The result is shown below:

TABLE 1

| | HDS-R scores | |
|---|---|---|
| Trialists | Score before administration | Administration period/score |
| A: 75-year-old male | 18 | 3 months/21 |
| B: 80-year-old female | 16 | 3 months/17 |
| C: 82-year-old male | 16 | 3 months/17 |
| D: 75-year-old male | 16 | 3 months/21 |
| E: 77-year-old female | 13 | 3 months/21 |
| F: 82-year-old female | 20 | 4 months/23 |
| G: 84-year-old male | 5 | 2.5 months/10.5 |

G: Simultaneous use of Rivastach patch 9 mg + Gramalil 1 tablet/day

As can be understood from Table 1, the score rose by 1 to 8 points for short periods of 2.5 to 4 months though there is a variation in data. It is conceivable that the improvement effect after such a short period is because the composition of the present invention promotes remyelination, promote the activity of α-secretase, repress the expression of β-secretase and act in a comprehensive way.

INDUSTRIAL APPLICABILITY

The present invention enables the safe and prompt treatment and/or prevention for Alzheimer's disease.

What is claimed is:

1. A composition for treatment of Alzheimer's disease in unit dose comprising:
    at least one compound selected from the group consisting of glycerophosphocholine and pharmacologically acceptable salts thereof as a first active ingredient; and
    hesperidin and narirutin as a second active ingredient,
    the composition promoting remyelination and α-secretase activity and repressing β-secretase expression.

2. The composition for treatment of Alzheimer's disease according to claim 1, which comprises 10 to 120 mg of the first active ingredient and 30 to 100 mg of the second active ingredient as a daily dosage for an adult.

3. The composition for treatment of Alzheimer's disease according to claim 1,
    wherein the hesperidin and the narirutin are in a form of Chinpi derived from Citrus unshiu or an extract of the Chinpi.

4. The composition for treatment of Alzheimer's disease according to claim 1, which is administered as health food.

* * * * *